United States Patent
Ashwood et al.

[11] Patent Number: 6,130,331
[45] Date of Patent: Oct. 10, 2000

[54] CHEMICAL SYNTHESIS OF A CHIRAL 1,4-OXAZIN-2-ONE

[75] Inventors: Michael Stewart Ashwood, Bishops Stortford; Ian Frank Cottrell, Hertford; Brian Christopher Bishops, Bishops Stortford; John Simon Edwards, Ware, all of United Kingdom

[73] Assignee: Merck Sharp & Dohme Ltd., Hoddesdon, United Kingdom

[21] Appl. No.: 09/391,939

[22] Filed: Sep. 8, 1999

[30] Foreign Application Priority Data

Sep. 11, 1998 [GB] United Kingdom .................. 9819888

[51] Int. Cl.⁷ ..................... C07D 265/30; C07D 265/32
[52] U.S. Cl. ................. 544/106; 544/106; 544/107; 544/173
[58] Field of Search ..................... 544/106, 107, 544/173

[56] References Cited

U.S. PATENT DOCUMENTS 6,046,325  4/2000  Ashwood et al. ........................ 544/173

FOREIGN PATENT DOCUMENTS 0577394  6/1993  European Pat. Off. .

*Primary Examiner*—Mukund J. Shah
*Assistant Examiner*—Ben Schroeder
*Attorney, Agent, or Firm*—J. Eric Thies; David L. Rose

[57] ABSTRACT

The present invention relates to a process for the preparation of substantially pure N-((S)-(−)-α-methylbenzyl)-3-(S)-(4-fluorophenyl)-1,4-oxazin-2-one hydrochloride, which comprises selectively crystallising the (S,S)-diastereomer as the hydrochloride salt from a mixture of the (S,R)- and (S,S)-diastereomers in an organic solvent, and collecting the resultant crystalline product.

22 Claims, No Drawings

CHEMICAL SYNTHESIS OF A CHIRAL 1,4-OXAZIN-2-ONE

CROSS REFERENCE TO RELATED APPLICATIONS

This application claims priority under 35 U.S.C. 119 from Great Britain Application No. 9819888.0, filed Sep. 11, 1998.

The present invention relates to a process for the preparation of a chiral 1,4-oxazin-2-one derivative which is useful as an intermediate in the preparation of certain therapeutic agents. In particular, the present invention provides a process for the preparation of optically pure N-((S)-(−)-α-methylbenzyl)-3-(S)-(4-fluorophenyl)-1,4-oxazin-2-one which is an intermediate in the preparation of pharmaceutical compounds which are substance P (or neurokinin-1) receptor antagonists.

European patent specification No. 0 577 394-A (published 5th January 1994) describes the preparation of benzyloxazinones by a two-step process starting from optically pure glycine derivatives. Control of process parameters (e.g. reaction time, temperature, moisture content) is necessary to prevent racemisation in these steps. With reference to Example 59 in EP-0 577 394-A, the N-benzyl-1,4-oxazin-2-one is prepared as follows:

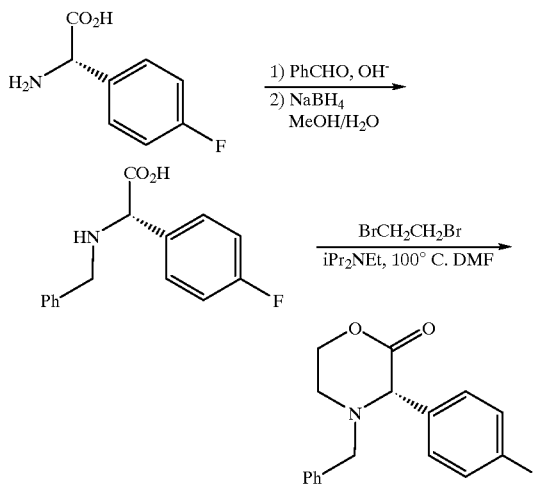

Furthermore, the optically pure (S)-(4-fluorophenyl) glycine is disclosed as having been prepared by means of a four-step asymmetric synthesis process which is based upon the procedure for the asymmetric synthesis of α-amino acids described by D. A. Evans et al., *J. Am. Chem. Soc.*, (1990) 112, 4011–4030.

The complexity of this four-step process combined with the sensitive nature of the protection and double alkylatin reactions to give the desired 1,4-oxazin-2-one, renders these prior art syntheses impracticable when attempted on anything other than a laboratory scale.

More recently, in British Patent Specification No. 2,301, 588-A (published Dec. 11, 1996) an alternative procedure was proposed which utilized racemic N-benzyl-3-(4-fluorophenyl)-1,4-oxazin-2-one as starting material and in a minimum of steps afforded product of high enantiomeric purity in high yield.

Resolution of racemic N-benzyl-3-(4-fluorophenyl)-1,4-oxazin-2-one was achieved using (−)-3-bromocamphor-8-sulphonic acid (also referred to as (−)-3-BCS) in the presence of a racemising agent. Whilst this is an effective method for obtaining substantially pure N-benzyl-3-(S)-(4-fluorophenyl)-1,4-oxazin-2-one, the use of (−)-3-BCS on a large scale is expensive. Furthermore, large quantities of (−)-3-BCS are not readily available.

It will be appreciated that chiral 3-(S)-(4-fluorophenyl)-1,4-oxazin-2-one derivatives are important intermediates for a particularly useful class of therapeutic agents. As such, there is a need for the development of a process which is readily amenable to scale-up, uses cost-effective and readily available reagents and which is therefore capable of practical application to the manufacturing plant.

The present invention accordingly provides a convenient, efficient process for preparing a chiral oxazinone derivative which involves the preparation of an a-methylbenzyl chiral auxiliary, thereby generating a pair of diastereomers. The physical properties of the diastereomers differ, and it is possible to separate their hydrochloride salts by selective crystallisation. As a result, the desired product, namely N-(α-methylbenzyl)-3-(S)-(4-fluorophenyl)-1,4-oxazin-2-one, can be isolated as the hydrochloride salt as a single diastereomer. The chiral auxiliary is preferably the (S)-(−)-α-methylbenzyl chiral auxiliary. In a further aspect of the present invention, the selective crystallisation is carried out under conditions which epimerise the undesired diastereomer to give the desired isomer. This combination of selective crystallisation and in situ epimerisation results in the highly efficient preparation of N-((S)-(−)-α-methylbenzyl)-3-(S)-(4-fluorophenyl)-1,4-oxazin-2-one, with high yield (greater than 80%) and high diastereomeric excess (greater than 97%).

Thus, in a first aspect of the present invention, there is provided a process for the preparation of substantially pure N-((S)-(−)-α-methylbenzyl)-3-(S)-(4-fluorophenyl)-1,4-oxazin-2-one hydrochloride, which comprises selectively crystallising the (S,S)-diastereomer as the hydrochloride salt from a mixture of the (S,R)- and (S,S)-diastereomers in an organic solvent, and collecting the resultant crystalline product.

According to a preferred aspect of the present invention, the process is effected in an organic solvent in the presence of hydrogen chloride gas to epimerise the (S,R)-diastereomer to the (S,S)-diastereomer in situ. In particular, the organic solvent may be saturated with hydrogen chloride gas.

Suitable organic solvents of use in the present invention include isopropyl acetate, ethyl acetate and toluene. The use of isopropyl acetate is particularly preferred.

Preferably the crystallisation (and in situ epimerisation) is effected at an elevated temperature, for example, between 70° C. and the reflux temperature of the solvent, and most preferably at reflux.

The hydrochloride salt of the (S,S)-diastereomer is a novel compound, thus, in a further or alternative aspect of the present invention, there is provided the compound N-((S)-(−)-α-methylbenzyl)-3-(S)-(4-fluorophenyl)-1,4-oxazin-2-one in the form of its hydrochloride salt.

The mixture of (S,R) and (S,S)-diastereomers may be prepared by a variety of methods, thus, according to a further or alternative aspect of the present invention, there is provided a process (A) for the preparation of substantially pure N-((S)-(−)-α-methylbenzyl)-3-(S)-(4-fluorophenyl)-1,4-oxazin-2-one, hydrochloride, as described above, wherein the mixture of (S,R)- and (S,S)-diastereomers is prepared by the reaction of 4-fluorophenylglyoxal with N-((S)-(−)-α-methylbenzyl)ethanolamine (otherwise known as 2-(1-(S)-phenylethyl)aminoethanol) in the presence of an acid.

In this reaction, the glyoxal is conveniently either anhydrous or hydrated. Suitable acids of use in the reaction include organic acids and inorganic acids. Where an inorganic acid is used, it is preferably anhydrous. Aliphatic and aromatic organic acids are preferred. Examples of suitable acids include aliphatic organic acids such as acetic acid, propanoic acid, butanoic acid and trifluoroacetic acid, aromatic organic acids such as benzoic acid, and anhydrous inorganic acids such as hydrobromic acid and hydrochloric acid. Acetic acid is particularly preferred.

The reaction is conveniently effected in an organic solvent, for example, ethyl acetate, isopropyl acetate or toluene. Isopropyl acetate is particularly preferred.

In a yet further and alternative aspect of the present invention, there is provided a process (B) for the preparation of substantially pure N-((S)-(–)-α-methylbenzyl)-3-(S)-(4-fluorophenyl)-1,4-oxazin-2-one, hydrochloride, as described above, wherein the mixture of (S,R)- and (S,S)-diastereomer is prepared by the acid catalysed cyclisation and hydrolysis of N-(2-hydroxyethyl)-N-(1-(S)-phenylethyl)-1-cyano-(4-fluorophenyl)methylamine.

Suitable acids of use in this reaction include mineral acids, especially hydrochloric acid. The reaction is conveniently effected in a suitable solvent such as an ether, for example, dioxane, or an ester, for example, isopropyl acetate, or water, or a mixture thereof. Dioxane, isopropyl acetate or isopropyl acetate/water are particularly preferred. The reaction is conveniently effected at room temperature.

The hydroxynitrile intermediate described above may be prepared, for example, by the reaction of 1-cyano-1-(4-fluorophenyl)methanol with (S)-α-methylbenzylethanolamine. The reaction is conveniently effected in an organic solvent such as an alcohol, for example, methanol, at a temperature between 40° and 50° C.

The cyanohydrin intermediate described above may be prepared, for example, by the reaction of 4-fluorobenzaldehyde with sodium metabisulfite, followed by sodium cyanide. The reaction is conveniently effected in an organic solvent such as an alcohol, for example, methanol, or water, or a mixture thereof, conveniently at room temperature.

In a yet further and alternative aspect of the present invention, there is provided a process (C) for the preparation of substantially pure N-((S)-(–)-α-methylbenzyl)-3-(S)-(4-fluorophenyl)-1,4-oxazin-2-one, hydrochloride, as described above, wherein the mixture of (S,R)- and (S,S)-diastereomers is prepared by the reaction of N-((S)-α-methylbenzyl)-4-fluorophenylglycine with 1,2-dibromoethane in the presence of a base.

Suitable bases of use in this reaction include organic bases, such as diisopropylethylamine, and inorganic bases such as sodium hydroxide. The reaction is conveniently effected in a suitable solvent such as dimethylformamide or an ester, for example isopropyl acetate. Dimethylformamide is preferred. The reaction is conveniently effected at an elevated temperature between 110° and 140° C., for example, at about 125° C.

The glycine intermediate described above may be prepared, for example, by reaction of (S)-α-methylbenzylamine with 1-cyano-1-(4-fluorophenyl) methanol (described above as an intermediate under process (B)), followed by hydrolysis of the nitrile moiety. Hydrolysis may be effected using acid or base, especially, for example, aqueous sodium hydroxide containing 6–12% hydrogen peroxide. It may be more desirable to proceed via the corresponding amide, in which case the nitrile intermediate is initially treated with, for example, hydrogen peroxide in the presence of a base such as potassium carbonate. Subsequent conversion of the aminoamide to the amino acid may be effected using, for example, sodium hydroxide. The reaction is conveniently effected in an organic solvent such as an ester, for example, isopropyl acetate, or an alcohol, for example, methanol, or a mixture thereof, conveniently at room temperature for the reaction betwen (S)-α-methylbenzylamine and the cyanohydrin, at a temperature below 40° C. for the conversion to the aminoamide intermediate, and at reflux for the hydrolysis to the glycine intermediate.

The following non-limiting examples illustrate processes according to the present invention. As used herein, diastereomeric excess is measured using the following HPLC system:

Zorbax RX C-8 250×4.6 mm

System A: 0.1% phosphoric acid

System B: acetonitrile

Isocratic 50% A/50% B 1.0 ml/minute 220 nm

Ambient temperature retention time for S,S isomer=20.5 minutes retention time for S,R isomer=22.5 minutes

EXAMPLE 1

Preparation of N-((S)-(–)-α-methylbenzyl)-3-(S)-(4-fluorophenyl)-1,4-oxazin-2-one hydrochloride from 4-fluorophenylglyoxal hydrate and (S)-2-(1-phenylethyl) ethanolamine (Process A)

A mixture of 2-(1-(S)-phenylethyl)ethanolamine([CAS 66849-29-4], 5g, 30 mmol), 4-fluorophenylglyoxal hydrate (5.7 g, 33 mmol) and acetic acid (10 ml) in isopropyl acetate (50 ml) was heated under reflux for 2.5 hours. The mixture was cooled, diluted with isopropyl acetate (100 ml) and washed with water (2×50 ml), aqueous sodium bicarbonate (2×50 ml) then water (25 ml). The solution was filtered then concentrated to low volume by distillation in a vacuum at 50° C.

The mixture was flushed with isopropyl acetate (2×100 ml) and the final volume adjusted to 150 ml with isopropyl acetate. The solution was heated to reflux temperature and saturated with HCl gas. After 8 hours the resultant slurry was cooled to room temperature and the product collected by filtration and washed with isopropyl acetate (50 ml). The product was dried in a vacuum at 50° C. to give N-((S)-(–)-α-methylbenzyl)-3-(S)-(4-fluorophenyl)-1,4-oxazin-2-one hydrochloride as a white crystalline solid. (8.76 g) 97.4% d.e. by HPLC, m.p. 202–204° C.

EXAMPLE 2

Preparation of N-((S)-(–)-α-methylbenzyl)-3-(S)-(4-fluorophenyl)-1,4-oxazin-2-one hydrochloride from 4-fluorobenzaldehyde and (S)-α-methylbenzylethanolamine (Process B)

A solution of 4-fluorobenzaldehyde (12.4 g) in methanol (3.6 ml) was added to a solution of sodium metabisulfite (10.3 g) in water (86 ml). Sodium cyanide (5.1 g) was added and the mixture stirred for 60 minutes at ambient temperature. A solution of (S)-α-methylbenzylethanolamine (18.34 g) in methanol (20 ml) was added and the mixture was heated at 30° C. overnight, then at 40° C. for 3 hours and 50° C. for 3 hours. The mixture was cooled and partitioned between water (41 ml) and isopropyl acetate (107 ml). The organic extract was washed with water (2×41 ml) and dried by azeotropic distillation.

A solution of HCl gas in isopropyl acetate (10% w/v, 36.5 ml) was added, followed by water (0.36 g), followed by a solution of HCl gas in isopropyl acetate (10% w/v, 36.5 ml). The mixture was stirred for 3 days then filtered to isolate the title compound (11.7 g) 97.6% d.e. by HPLC.

EXAMPLE 3

Preparation of N-((S)-(–)-α-methylbenzyl)-3-(S)-(4-fluorophenyl)-1,4-oxazin-2-one hydrochloride from 4-fluorobenzaldehyde and (S)-α-methylbenzylamine (Process C)

A solution of 4-fluorobenzaldehyde (1.02 kg, 8.2 mol) in methanol (1 liter) was added to a solution of sodium metabisulfite (842 g) in water (7.3 liters) and aged for 30 minutes. Sodium cyanide (414 g) was added and rinsed in with water (400 ml). After 45 minutes a solution of (S)-α-methylbenzylamine (1.0 kg) in methanol (600 ml) was added and the mixture was aged overnight at room temperature. The mixture was partitioned between water (3.5 liters) and isopropyl acetate (5 liters). The organic phase was washed with water (3.5 liters) and concentrated in a vacuum. The residue was dissolved in dimethylsulfoxide (7.6 liters) and potassium carbonate (444 g) added. 27% aq. Hydrogen peroxide (1.28 liters) was added over 30 minutes at <30° C. The mixture was then heated overnight at 40° C. The mixture was partitioned between water (16 liters) and isopropyl acetate (11 liters). The organic layer was washed with water (2×4.5 liters) and concentrated to an oil (2.14 kg, 96%). This crude amide was dissolved in IMS (4 liters) and a solution of sodium hydroxide (460 g) in water (11.3 liters) was added. The solution was heated under reflux for 12 hours then concentrated by distillation to remove IMS. The mixture was washed with ethylene glycol (2×2.2 liters) and the aqueous layer was acidified to pH 6.5 with aqueous HCl. The product, N-((S)-α-methylbenzyl)-4-fluorophenylglycine (1.7 kg, 75% yield from 4-fluorobenzaldehyde) was isolated by filtration. N-((S)-α-methylbenzyl)-4-fluorophenylglycine (1.4 kg), diisopropylethylamine (1.99 l, 2.2 eq.) and 1,2-dibromoethane (3.78 l, 8.5 eq.) were combined in dimethylformamide (24.5 liters) and heated at 125° C. for 8 hours. The mixture was concentrated in a vacuum and partitioned between isopropyl acetate (15 liters) and water (15 liters). The organics were washed with water (15 liters) and evaporated to give the crude oxazinone as a dark-coloured oil (1.44 kg).

The dark oil was dissolved in isopropyl acetate (10.4 liters) and heated to 85° C. HCl gas was bubbled though the mixture at 80°–85° C. for 6 hours, the flow stopped and the mixture allowed to cool slowly to 23° C. The slurry was filtered and the solid was washed with isopropyl acetate. The solid was dried to give N-((S)-(–)-α-methylbenzyl)-3-(S)-(4-fluorophenyl)-1,4-oxazin-2-one hydrochloride as a light brown solid (970 g) d.e. 98.4% by HPLC.

What we claim is:

1. A process for the preparation of substantially pure N-((S)-(–)-α-methylbenzyl)-3-(S)-(4-fluorophenyl)-1,4-oxazin-2-one hydrochloride, which comprises selectively crystallizing the (S,S)-diastereomer as the hydrochloride salt from a mixture of the (S,R)- and (S,S)-diastereomers in an organic solvent, and collecting the resultant crystalline product.

2. A process as claimed in claim 1 wherein said process is effected in an organic solvent in the presence of hydrogen chloride gas to epimerize the (S,R)-diastereomer to the (S,S)-diastereomer in situ.

3. A process as claimed in claim 1 wherein said organic solvent is selected from the group consisting of isopropyl acetate, ethyl acetate and toluene.

4. A process as claimed in claim 3 wherein said organic solvent is isopropyl acetate.

5. A process as claimed in claim 1 wherein said crystallization and in situ epimerization are effected at an elevated temperature.

6. A process as claimed in claim 5 wherein said elevated temperature is between 70° C. and the reflux temperature of the solvent.

7. The compound N-((S)-(–)-α-methylbenzyl)-3-(S)-(4-fluorophenyl)-1,4-oxazin-2-one in the form of its hydrochloride salt.

8. A process as claimed in claim 1 wherein said mixture of (S,R)- and (S,S)-diastereomers is prepared by the reaction of 4-fluorophenylglyoxal with N-((S)-(–)-α-methylbenzyl) ethanolamine in the presence of an acid.

9. A process as claimed in claim 8 wherein said acid is selected from the group consisting of acetic acid, propanoic acid, butanoic acid, trifluoroacetic acid, benzoic acid, hydrobromic acid and hydrochloric acid.

10. A process as claimed in claim 9 wherein said acid is acetic acid.

11. A process as claimed in claim 8 wherein said process is effected in an organic solvent selected from the group consisting of ethyl acetate, isopropyl acetate and toluene.

12. A process as claimed in claim 11 wherein said organic solvent is isopropyl acetate.

13. A process as claimed in claim 1 wherein said mixture of (S,R)- and (S,S)-diastereomer is prepared by the acid catalyzed cyclization and hydrolysis of N-(2-hydroxyethyl)-N-(1-(S)-phenylethyl)-1-cyano-(4-fluorophenyl) methylamine.

14. A process as claimed in claim 13 wherein said acid is a mineral acid.

15. A process as claimed in claim 14 wherein said mineral acid is hydrochloric acid.

16. A process as claimed in claim 13 wherein said process is effected in a solvent selected from the group consisting of an ether, an ester, water, and mixtures thereof.

17. A process as claimed in claim 16 wherein said solvent is selected from the group consisting of dioxane, isopropyl acetate and isopropyl acetate/water.

18. A process as claimed in claim 1 wherein said mixture of (S,R)- and (S,S)-diastereomers is prepared by the reaction of N-((S)-α-methylbenzyl)-4-fluorophenylglycine with 1,2-dibromoethane in the presence of a base.

19. A process as claimed in claim 18 wherein said base is selected from the group consisting of organic bases and inorganic bases.

20. A process as claimed in claim 19 wherein said base is selected from the group consisting of diisopropylethylamine and sodium hydroxide.

21. A process as claimed in claim 18 wherein said process is effected in a solvent selected from the group consisting of dimethylformamide and isopropyl acetate.

22. A process as claimed in claim 18 wherein said process is effected at an elevated temperature between 110° and 140° C.

* * * * *